(12) United States Patent
Brumfield et al.

(10) Patent No.: US 8,715,283 B2
(45) Date of Patent: May 6, 2014

(54) FRACTURE FIXATION DEVICE

(75) Inventors: David L. Brumfield, Collierville, TN (US); Nicholas S. Ritchey, Collierville, TN (US); Nathaniel Kelley Grusin, Germantown, TN (US); Sied W. Janna, Memphis, TN (US); Henry B. Faber, Memphis, TN (US); Gene E. Austin, Bartlett, TN (US)

(73) Assignee: Smith & Nephew, Inc., Memphis, TN (US)

( * ) Notice: Subject to any disclaimer, the term of this patent is extended or adjusted under 35 U.S.C. 154(b) by 981 days.

(21) Appl. No.: 12/377,171

(22) PCT Filed: Aug. 14, 2007

(86) PCT No.: PCT/US2007/075913
§ 371 (c)(1),
(2), (4) Date: Feb. 11, 2009

(87) PCT Pub. No.: WO2008/022136
PCT Pub. Date: Feb. 21, 2008

(65) Prior Publication Data
US 2010/0249852 A1   Sep. 30, 2010

Related U.S. Application Data

(60) Provisional application No. 60/822,339, filed on Aug. 14, 2006.

(51) Int. Cl.
*A61B 17/58* (2006.01)
*A61B 17/74* (2006.01)
*A61B 17/76* (2006.01)

(52) U.S. Cl.
USPC .................................................. 606/64

(58) Field of Classification Search
USPC ........................... 606/62–68, 300–321
See application file for complete search history.

(56) References Cited

U.S. PATENT DOCUMENTS

| | | | | |
|---|---|---|---|---|
| 2,381,050 | A * | 8/1945 | Hardinge | 606/65 |
| 4,636,123 | A * | 1/1987 | Herb | 411/55 |
| 5,032,125 | A * | 7/1991 | Durham et al. | 606/62 |
| 5,041,114 | A * | 8/1991 | Chapman et al. | 606/62 |
| 6,443,954 | B1 * | 9/2002 | Bramlet et al. | 606/62 |
| 7,527,627 | B2 | 5/2009 | Ferrante et al. | |
| 7,534,244 | B2 | 5/2009 | Ferrante et al. | |
| 7,780,667 | B2 | 8/2010 | Watanabe et al. | |
| 7,799,030 | B2 | 9/2010 | Watanabe et al. | |
| 7,883,509 | B2 | 2/2011 | Ferrante et al. | |
| 7,931,652 | B2 | 4/2011 | Ferrante et al. | |
| 2004/0210227 | A1 * | 10/2004 | Trail et al. | 606/73 |

(Continued)

*Primary Examiner* — Nicholas Woodall
(74) *Attorney, Agent, or Firm* — Krieg DeVault LLP (57) ABSTRACT

A fracture fixation system 10, 20, 30, 40, 50, 58, 70 for a fractured bone having at least two bone fragments is disclosed. The fracture fixation system 10, 20, 30, 40, 50, 58, 70 includes an orthopaedic implant 11, 21, 31, 41, 51, 60, 71, an engaging member 12, 22, 32, 43, 45, 52, 62, 72 adapted to gain purchase in at least one bone fragment, and means for applying a force to the engaging member such that the at least two bone fragments are placed in compression and prevented from rotating relative to the orthopaedic implant. The engaging member 12, 22, 32, 43, 45, 52, 62, 72 is disposed relative to the orthopaedic implant 11, 21, 31, 41, 51, 60, 71. The orthopaedic implant 11, 21, 31, 41, 51, 60, 71 may take the form of an intramedullary device, a compression plate, or a deployable material.

16 Claims, 11 Drawing Sheets

(56) References Cited

U.S. PATENT DOCUMENTS

| | | | |
|---|---|---|---|
| 2005/0055024 A1* | 3/2005 | James et al. | 606/64 |
| 2006/0155281 A1* | 7/2006 | Kaup et al. | 606/65 |
| 2008/0188853 A1 | 8/2008 | Ferrante et al. | |
| 2009/0209961 A1 | 8/2009 | Ferrante et al. | |
| 2010/0022764 A1 | 1/2010 | Otoshi et al. | |
| 2011/0060337 A1 | 3/2011 | Ferrante et al. | |
| 2011/0087228 A1 | 4/2011 | Ferrante et al. | |

* cited by examiner

FRACTURE FIXATION DEVICE

CROSS-REFERENCE TO RELATED APPLICATIONS

This application is a National Phase of International Application No. PCT/US2007/075913 filed Aug. 14, 2007 and claims the benefit of U.S. Provisional Application No. 60/822,339 filed Aug. 14, 2006. The disclosure of each prior application is incorporated by reference in its entirety.

STATEMENT REGARDING FEDERALLY SPONSORED RESEARCH OR DEVELOPMENT

Not Applicable.

APPENDIX

Not Applicable.

BACKGROUND OF THE INVENTION

1. Field of the Invention

Embodiments of the present invention generally relate to systems for coupling bone portions across a fracture and, in some embodiments, to intramedullary nail or plate and screw assemblies or other stabilizing structures, deployable materials, and/or fastening assemblies used to treat fractures of long bones, such as the femur, humerus, tibia, and various periarticular fractures of these and other bones.

2. Related Art

There are a variety of devices used to treat fractures of the femur, humerus, tibia, and other long bones. For example, fractures of the femoral neck, head, and intertrochanteric region have been successfully treated with a variety of compression screw assemblies, which include generally a compression plate having a barrel member, a lag screw and a compressing screw. In such systems, the compression plate is secured to the exterior of the femur, and the barrel member is inserted in a predrilled hole in the direction of the femoral head. The lag screw has a threaded end, or another mechanism for engaging bone, and a smooth portion. The lag screw is inserted through the barrel member so that it extends across the break and into the femoral head. The threaded portion engages the femoral head. The compression screw connects the lag screw to the plate. By adjusting the tension of the compression screw, the compression (reduction) of the fracture can be varied. The smooth portion of the lag screw is free to slide through the barrel member to permit the adjustment of the compression screw. Some assemblies of the prior art use multiple screws to prevent rotation of the lag screw relative to the compression plate and barrel member and also to prevent rotation of the femoral head on the lag screw.

Intramedullary nails in combination with lag screws or other screw assemblies have been successfully used to treat fractures of the femur, humerus, tibia, and other long bones as well. A significant application of such devices has been the treatment of femoral fractures. A typical prior art intramedullary nail may have one or more transverse apertures through its distal end to allow distal bone screws or pins to be screwed or otherwise inserted through the femur at the distal end of the intramedullary nail. This is called "locking" and secures the distal end of the intramedullary nail to the femur. In addition, a typical intramedullary nail may have one or more apertures through its proximal end to allow a lag screw assembly to be screwed or otherwise inserted through the proximal end of the intramedullary nail and into the femur. The lag screw is positioned across the fracture in the bone and an end portion of the lag screw engages the femoral head. An intramedullary nail can also be used to treat shaft fractures of the femur or other long bones.

As with compression hip screw systems, intramedullary nail systems are sometimes designed to allow compression screws and/or lag screws to slide through the nail and thus permit contact between or among the bone fragments. Contact resulting from sliding compression facilitates faster healing in some circumstances. In some systems, two separate screws are used in order to prevent rotation of the femoral head relative to the remainder of the femur, to prevent penetration of a single screw beyond the femoral head, and to prevent a single screw from tearing through the femoral neck and head. When an additional screw or pin is used, however, unequal forces applied to the separated screws or pins may cause the separate screws or pins to be pressed against the sides of the holes through which the separate screws or pins are intended to slide. This may result in binding, which may reduce or eliminate the sliding of the screws or pins through the nail. Conversely, a problem can result from excessive compression of the femoral head toward or into the fracture site. When excessive sliding compression occurs it may cause the femoral head to collapse into the trochanteric region of the femur.

In summary, and without limitation, the foregoing shows some of the shortcomings of the state of the art in this field. Among other things, what is needed is an orthopaedic implant system that includes a superior sliding screw or other mechanism for applying compression across a fracture. Some embodiments would also provide a sliding screw or other mechanism that obtains adequate bone purchase while reducing the incidence of cut-out, rotational instability, and excessive sliding. Additionally, an improved implant system could include a sliding screw (or other type of fastener/engaging member) in combination with intramedullary nails of various designs, in combination with plates, or in combination with various types of deployable materials. Combinations of any of these with each other or combinations of each other, and/or with other devices or combinations of them also present opportunities for advancement beyond the state of the art according to certain aspects of the present invention.

SUMMARY OF THE INVENTION

It is in view of the above problems that at least some of the embodiments of the present invention were developed. There is provided a fracture fixation system for a fractured bone having at least two bone fragments. The fracture fixation system includes an orthopaedic implant; an engaging member disposed relative to the orthopaedic implant, the engaging member adapted to gain purchase in at least one bone fragment; and means for applying a force to the engaging member such that the at least two bone fragments are placed in compression and prevented from rotating relative to the orthopaedic implant. The orthopaedic implant is selected from the group consisting of an intramedullary device, a compression plate, and a deployable material.

In one embodiment, the means for applying a force to the engaging member comprises an elongated member and a nut.

In one embodiment, the means for applying a force to the engaging member comprises a compression member that engages the engaging member and the orthopaedic implant.

In one embodiment, there is further provided an interlock member engaged with the engaging member, and the means for applying a force to the engaging member comprises a compression member that engages the engaging member and the orthopaedic implant.

In one embodiment, the means for applying a force to the engaging member comprises an interlock member and a nut.

In one embodiment, the means for applying a force to the engaging member comprises a compression member having a tapered thread depth.

In one embodiment, the means for applying a force to the engaging member comprises a compression member having a tapered diameter.

In one embodiment, the means for applying a force to the engaging member comprises an elongated member, a barrel, and a nut.

In one embodiment, the means for applying a force to the engaging member comprises a compression member and a barrel.

In one embodiment, the orthopaedic implant is an intramedullary device and wherein the means for applying a force to the engaging member comprises an elongate member having an enlarged end portion, a barrel, and a nut, the nut engaged with the barrel and the elongate member, the engaging member is cannulated and extends through the intramedullary device, the elongate member slides within the cannulation, the expanded end portion is received by an end portion of the engaging member, and the end portion deforms when a torque is applied to the nut.

In one embodiment, the barrel has internal flats which correspond to external flats on the engaging member.

In one embodiment, the orthopaedic implant is an intramedullary device and wherein the means for applying a force to the engaging member comprises a nut and an elongate member having an enlarged end portion, the engaging member has flats along its shaft, a fastener engages the flats and the intramedullary device to prevent rotation and limit the sliding of the engaging member, the nut engaged with the engaging member and the elongate member, the engaging member is cannulated and extends through the intramedullary device, the elongate member slides within the cannulation, the expanded end portion is received by an end portion of the engaging member, and the end portion deforms when a torque is applied to the nut.

In one embodiment, the orthopaedic implant is a compression plate and wherein the means for applying a force to the engaging member comprises an elongate member having an enlarged end portion, a barrel, and a nut, the nut engaged with the compression plate and the elongate member, the engaging member is cannulated and extends through the barrel, the elongate member slides within the cannulation, the expanded end portion is received by an end portion of the engaging member, and the end portion deforms when a torque is applied to the nut.

In one embodiment, the orthopaedic implant is an intramedullary device and wherein the means for applying a force to the engaging member comprises a compression member that engages a portion of the engaging member and a portion of the intramedullary device, and further comprising a fastener placed within the intramedullary device to lock the engaging member in a specific location.

In one embodiment, the orthopaedic implant is an intramedullary device, the system further comprising an interlock member engaged with the engaging member and the intramedullary device, and wherein the means for applying a force to the engaging member comprises a compression member that engages the engaging member and the intramedullary device.

In one embodiment, the orthopaedic implant is an intramedullary device and wherein the means for applying a force to the engaging member comprises an interlock member engaged with the engaging member and a nut adapted to apply a force to the interlock member to apply a force to the engaging member.

In one embodiment, the orthopaedic implant is a deployable material, and wherein the means for applying a force to the engaging member comprises a compression member and a barrel, the barrel receives at least a portion of the engaging member, the deployable material secures the engaging member and the barrel in respective bone fragments, and the compression member engages both the barrel and the engaging member.

In one embodiment, the orthopaedic implant is an intramedullary device and wherein the means for applying a force to the engaging member comprises a compression member having a tapering depth thread as it moves toward a distal tip end and adapted to engage an internal portion of the engaging member.

In one embodiment, the orthopaedic implant is an intramedullary device and wherein the means for applying a force to the engaging member comprises a compression member having a tapered diameter and adapted to engage an internal portion of the engaging member.

The invention has several advantages over prior devices and techniques. The invention allows for compression intraoperatively. Further, many of the embodiments prevent rotation of the relative bone fragments. This ensures that when placed into the bone, typically the proximal femur, the bone fragment(s) in the head of the femur will not rotate with respect to the orthopaedic implant and the shaft of the femur. Both of these advantages provide improved patient healing.

Further features, aspects, and advantages of the present invention, as well as the structure and operation of various embodiments of the present invention, are described in detail below with reference to the accompanying drawings.

BRIEF DESCRIPTION OF THE DRAWINGS

The accompanying drawings, which are incorporated in and form a part of the specification, illustrate embodiments of the present invention and together with the description, serve to explain the principles of the invention. In the drawings.

DETAILED DESCRIPTION OF THE EMBODIMENTS

Methods, devices and systems according to some embodiments of this invention allow treatment of bone fractures using devices configured to be implanted in or stabilize a first bone fragment and a fastening assembly. In embodiments shown in the accompanying drawings, the structure takes the form of a plate or other device for at least partial application to the outer surface of bone, or an implant for at least partial implantation within bone, such as an intramedullary nail, or a deployable material, although other structure may be employed. The implants depicted in the accompanying drawings include a proximal section having a transverse aperture, and an aperture substantially along their length. In some embodiments, the intramedullary nail may be similar to those known in the art and may have either a circular or non-circular cross-section. Embodiments may be made of any known biocompatible material, such as metal, composite, resorbable, etc.

Fastening assemblies of methods, devices and systems according to certain embodiments of the invention may include an engaging member and a compression device. The fastening assemblies may be adapted to be received in the transverse aperture of the implant in a sliding relationship, so that the fastening assembly is adapted to slide with respect to the transverse aperture, and thus apply compression to a fracture and for any other desired purpose. The engaging member may be adapted to gain purchase in a second bone fragment. The engaging member and the compression device may be configured so that the compression device interacts with a portion of the implant and also with a portion of the engaging member so that a surgeon may select a desired amount of compression between bone fragments. The compression device may be used to control the magnitude of the compressive force applied to the bone fragments. In some embodiments, adjustment of the compression device controls sliding of the engaging member relative to the implant and thereby enables controlled movement between the first and second bone fragments. In some embodiments, the compression device at least partially directly contacts the second bone fragment when implanted. In other embodiments, the compression devices do not directly contact the second bone fragment when implanted.

Some of the embodiments depicted in the accompanying drawings include an integrated interlocking screw or other type of interlocking member that may increase the stability and resistance to intra-operative and post-operative femoral head rotation, which may eliminate excessive sliding and the phenomena of medial and lateral migration of the two screw or other fasteners.

Figures 1, 2:
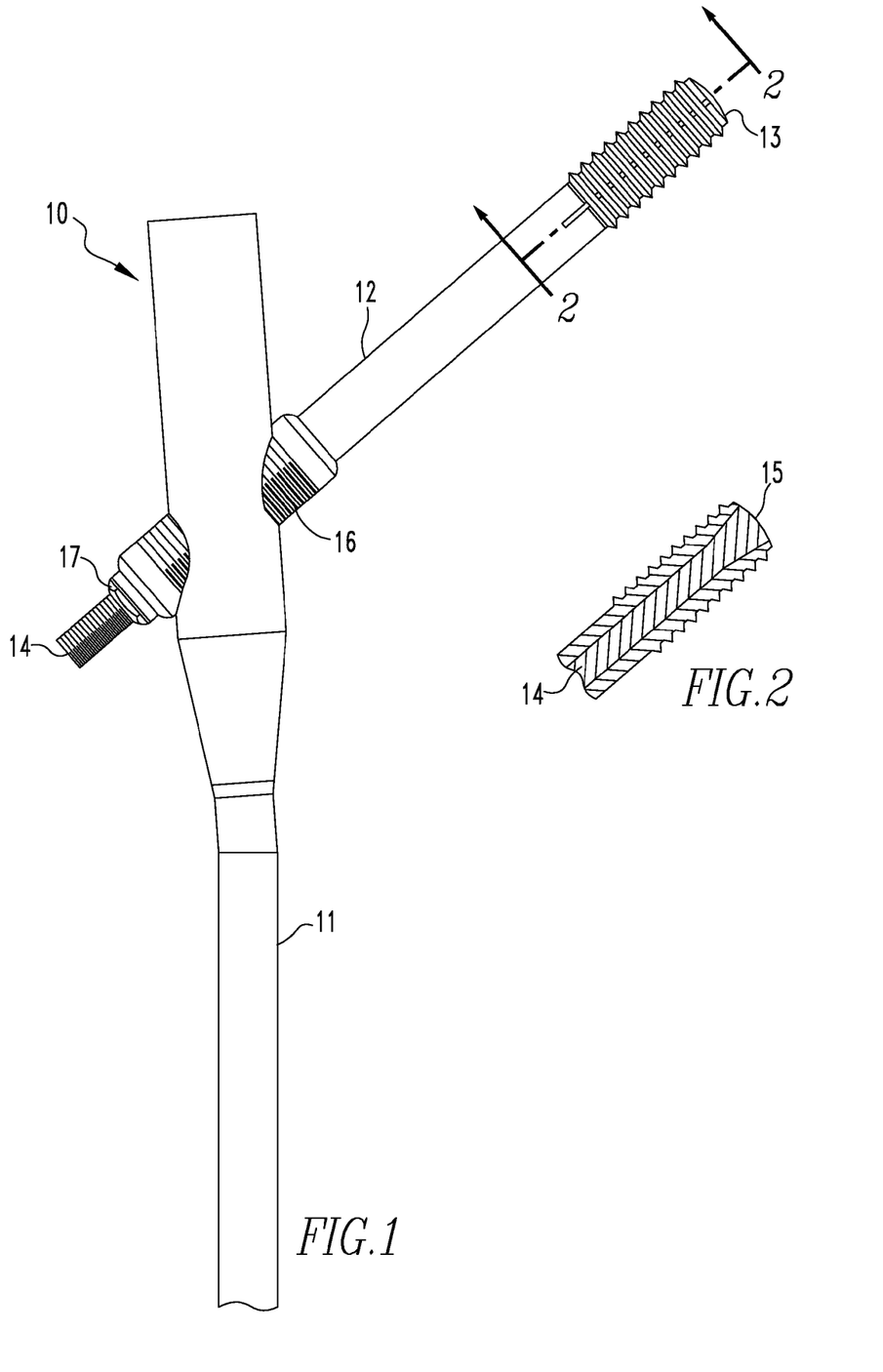
FIG. 1 is an anterior view of a fracture fixation system in a first embodiment.
FIG. 2 is a partial sectional view taken along lines 2-2 in FIG. 1.

Referring to the accompanying drawings in which like reference numbers indicate like elements, FIG. 1 illustrates a fracture fixation system 10 having an intramedullary device 11 and an engaging member 12. The engaging member 12 shown in FIG. 1 is cannulated and extends through the intramedullary device 11 into a head of a femur (not shown). An end portion 13 may be threaded and also may be formed in such a manner that it is expandable. As examples, the end portion 13 may be made from an elastic material or by forming slits thereon to allow for expansion when forced radially outward. In the embodiment shown in FIG. 2, inside of the engaging member 12 is another elongate member 14. The elongate member 14 may be cylindrical with an enlarged end portion 15 (best seen in FIG. 2). As examples, the end portion 15 may be tapered or conical. The elongate member 14 may also take on shapes that are oval, square, helical, or any other geometric shape. The engaging member 12 is inserted into the femoral head with the elongate member 14 contained inside of the engaging member 12 with its enlarged end portion 15 extending beyond or outside of the end of the engaging member 12. Elongate member 14 and engaging member 12 may be in sliding communication with one another and may be composed of any biocompatible material, such as stainless steel, titanium, cobalt chrome, metal alloy, composite material, ceramic material, or a bioresorbable material. As sown in FIG. 2, the end portion 13 of engaging member 12 is deformable so that it at least somewhat expands as elongate member 14 slides or is drawn through the end to engage enlarged end portion 15.

In some embodiments, the engaging member 11 includes a barrel 16. The barrel 16 may be threaded, have external grooves, textured or it may be smooth. The threaded barrel 16 depicted in FIG. 1 has internal flats or planar portions that correspond to external flats on the engaging member 12, although in other embodiments such external flats are unnecessary. The flats may enable the engaging member 12 to slide in the barrel 16 but prevents rotation of the engaging member 12 and the bone fragment that it is in. As examples, the barrel 16 may have an internal square, hex, or octagon shape that receives an external square, hex, or octagon shape of the engaging member 12. A set screw (not shown) may then, in some embodiments, be placed within the intramedullary device 11 and engage with the barrel 16 to limit the axial movement as well as the rotational movement. In other embodiments, the set screw is pre-assembled to the intramedullary device prior to its installation. In some embodiments, such a set screw or other structure may be used to limit only rotational movement but not axial movement, or vice-versa.

Some embodiments further include a nut 17 mounted about the elongate member 14 and abutting the barrel 16. After insertion of the engaging member 12 across a fracture, a surgeon may compress the fracture by applying a torque to the nut 17 that will cause the elongate member 14 to pull back through the engaging member 12. As the elongate member 14 moves through the engaging member 12 the enlarged end portion 15 forces the flexible end of the engaging member 12 to expand radially outward. This expansion enables the engaging member 12 to rigidly fix itself within the femoral head. The fixation may also prevent rotation of the engaging member 12 and the femoral head.

Figures 3, 4:
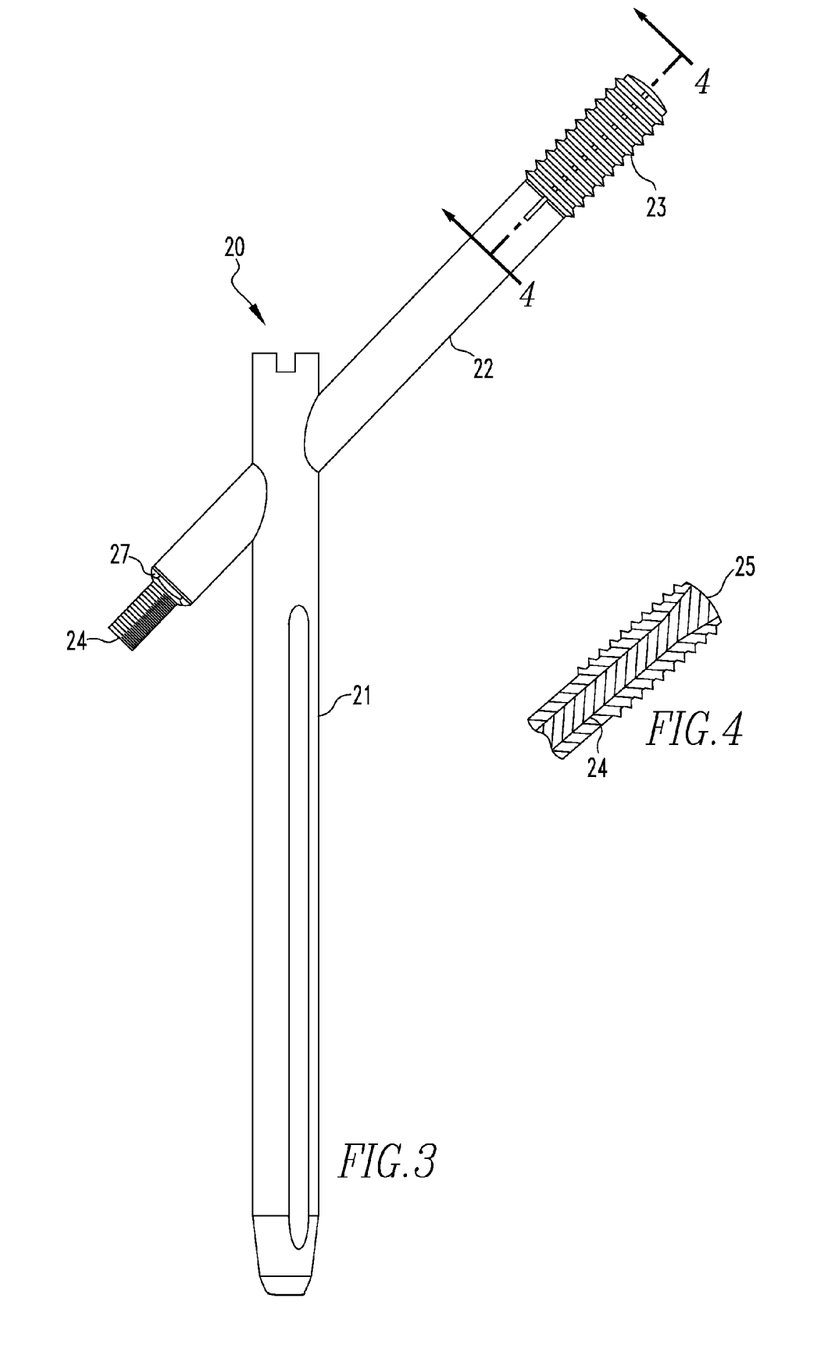
FIG. 3 is an anterior view of a fracture fixation system in a second embodiment.
FIG. 4 is a partial sectional view taken along lines 4-4 in FIG. 3

FIG. 3 illustrates an alternative embodiment of the fracture fixation system, generally indicated by reference numeral 20. The fracture fixation system 20 shown in FIG. 3 does not have a barrel. In the depicted embodiment an intramedullary device 21 is inserted into a medullary cavity (not shown). The femoral neck may then be prepared for inserting an engaging member 22. The area may be pre-drilled to allow easier insertion of the engaging member 22. In this embodiment the engaging member 22 has flats and/or grooves along its shaft. In some embodiments, a set screw (not shown) may then be inserted into the intramedullary device 21 and engage with the flats and/or grooves on the engaging member 22 to prevent rotation and limit the sliding of the engaging member 22. Expansion of an end portion 23 of the engaging member 22 may operate the same as described above in conjunction with FIG. 1 and includes an elongated member 24 and an enlarged end portion 25 (best seen in FIG. 4). In the embodiment depicted in FIG. 3, the nut 27 abuts the end of engaging member 22.

Figures 5, 6:
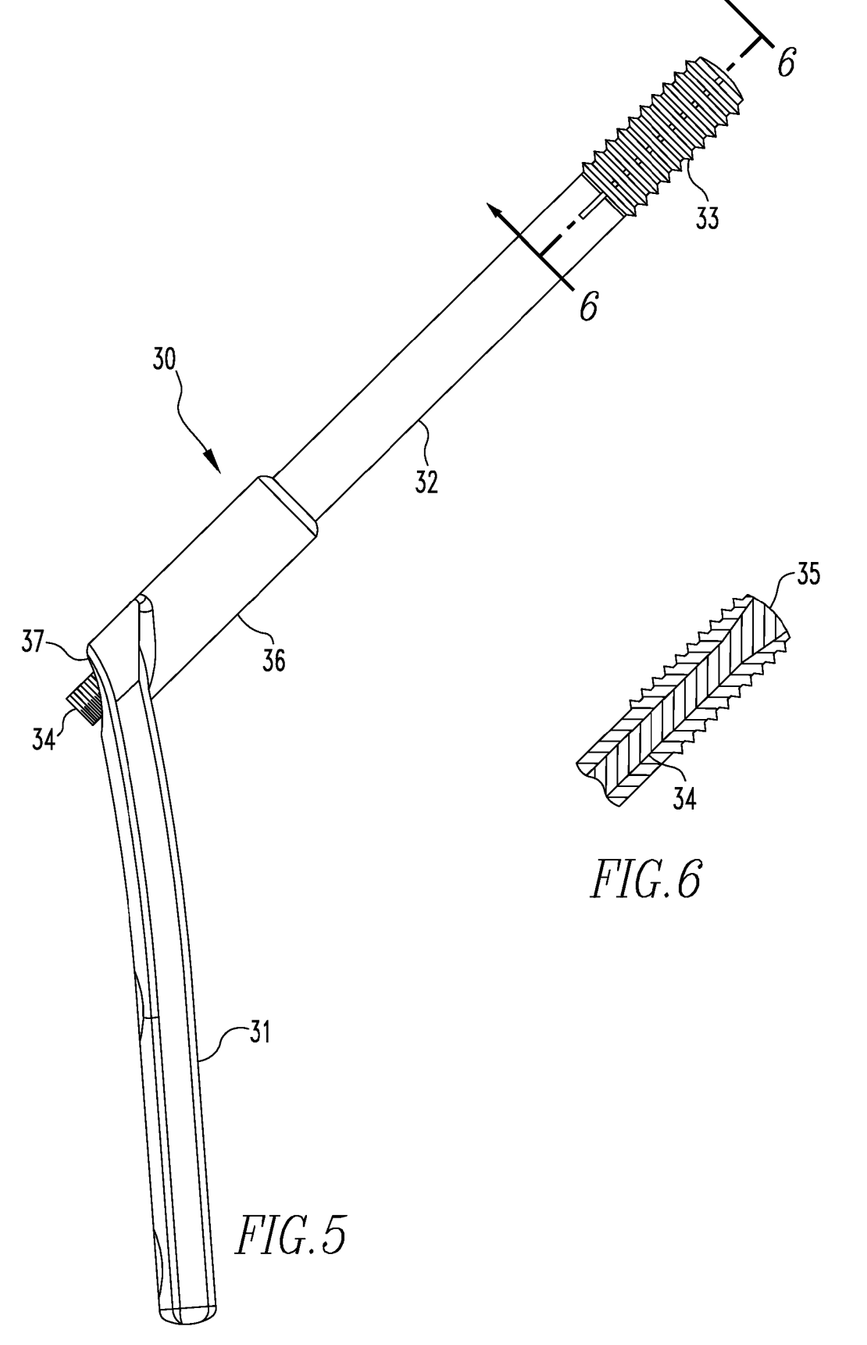
FIG. 5 is an anterior view of a fracture fixation system in a third embodiment
FIG. 6 is a partial sectional view taken along lines 6-6 in FIG. 5.

FIG. 5 illustrates yet another alternative embodiment of the fracture fixation system, generally indicated by reference numeral 30. In the embodiment shown in FIG. 5, the fracture fixation system includes a compression plate 31 instead of an intramedullary device. Those having ordinary skill in the art would understand that the compression plate and the intramedullary device are both orthopaedic implants and the particular device may be selected based upon fracture patterns and the discretion of the surgeon. The compression plate 31 shown may be secured to the exterior of the femur. For example, fasteners may be used to attach the compression plate 31 to the bone. In the embodiment depicted in FIG. 5, a barrel member 36 is inserted in a predrilled hole in the direction of the femoral head. The barrel member 36 may receive an engaging member 32 which may have a smooth shaft portion and a threaded end 33. The engaging member 32 may be inserted through the barrel member 36 so that it extends across the fracture and into the femoral head such that the threaded portion 33 engages the femoral head. The smooth shaft portion of the engaging member 32 may freely slide through the barrel member 36, in some embodiments, to permit the adjustment of a nut 37 to achieve intraoperative compression. In some embodiments, the barrel member 36 has internal flats that correspond with external flats on the engaging member 32 to prevent rotation. The fracture fixation system 30 shown may further include an elongate member 34 with an enlarged end portion 35 (best seen in FIG. 6), which in some embodiments may be at least somewhat similar to the structure depicted in FIGS. 1-4.

The compression plate 31 may be placed on the surface of the bone and then the femoral neck may be prepared for insertion of the barrel member 36 and engaging member 32. Once the barrel member 36 is inserted, the engaging member 32 may slide through the barrel member 36 and into the femoral neck or femoral head across the fracture site. Elongate member 34 may then be inserted into the engaging member 32 in the manner described for the embodiment shown in FIG. 1.

Figure 7:
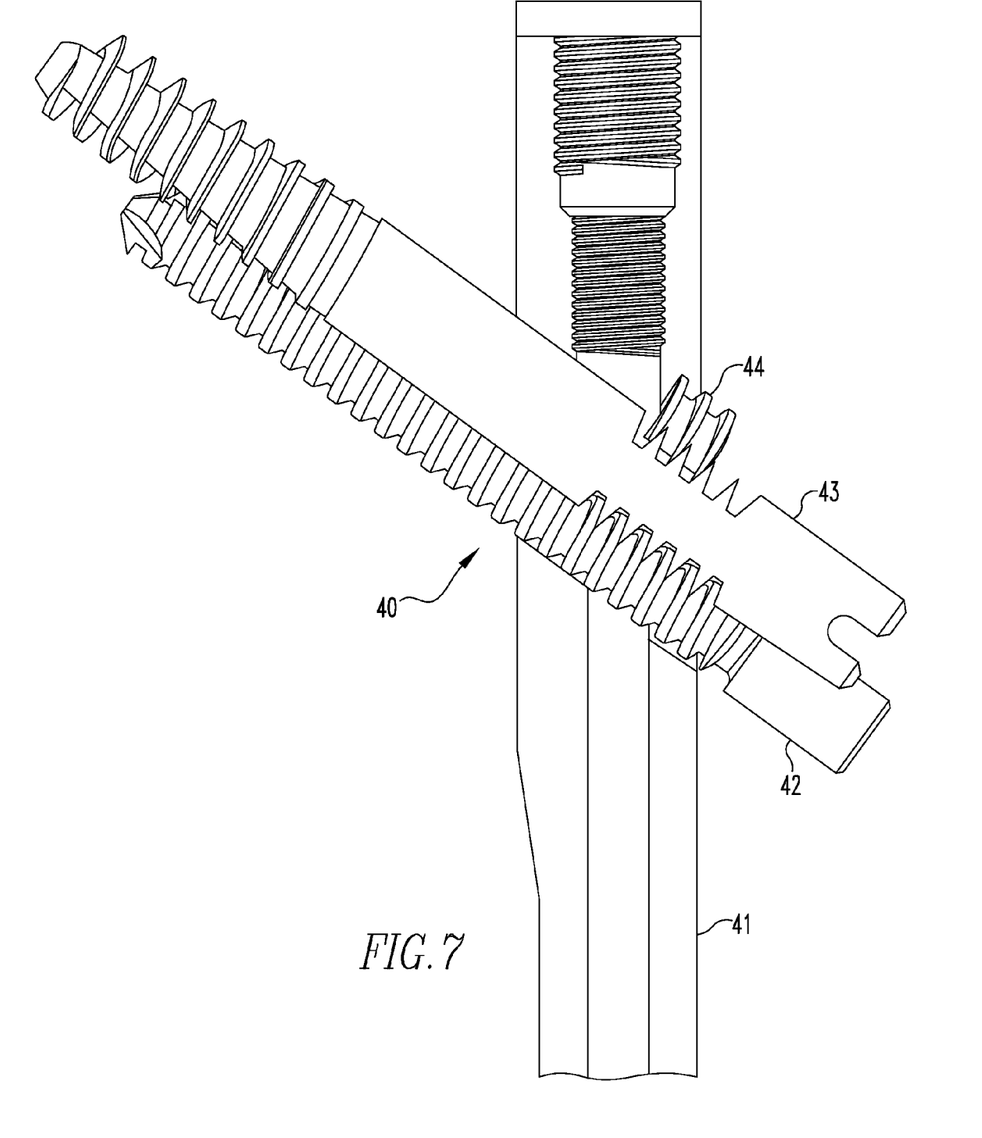
FIG. 7 is an anterior view of a fracture fixation system in a fourth embodiment.
Figure 8:
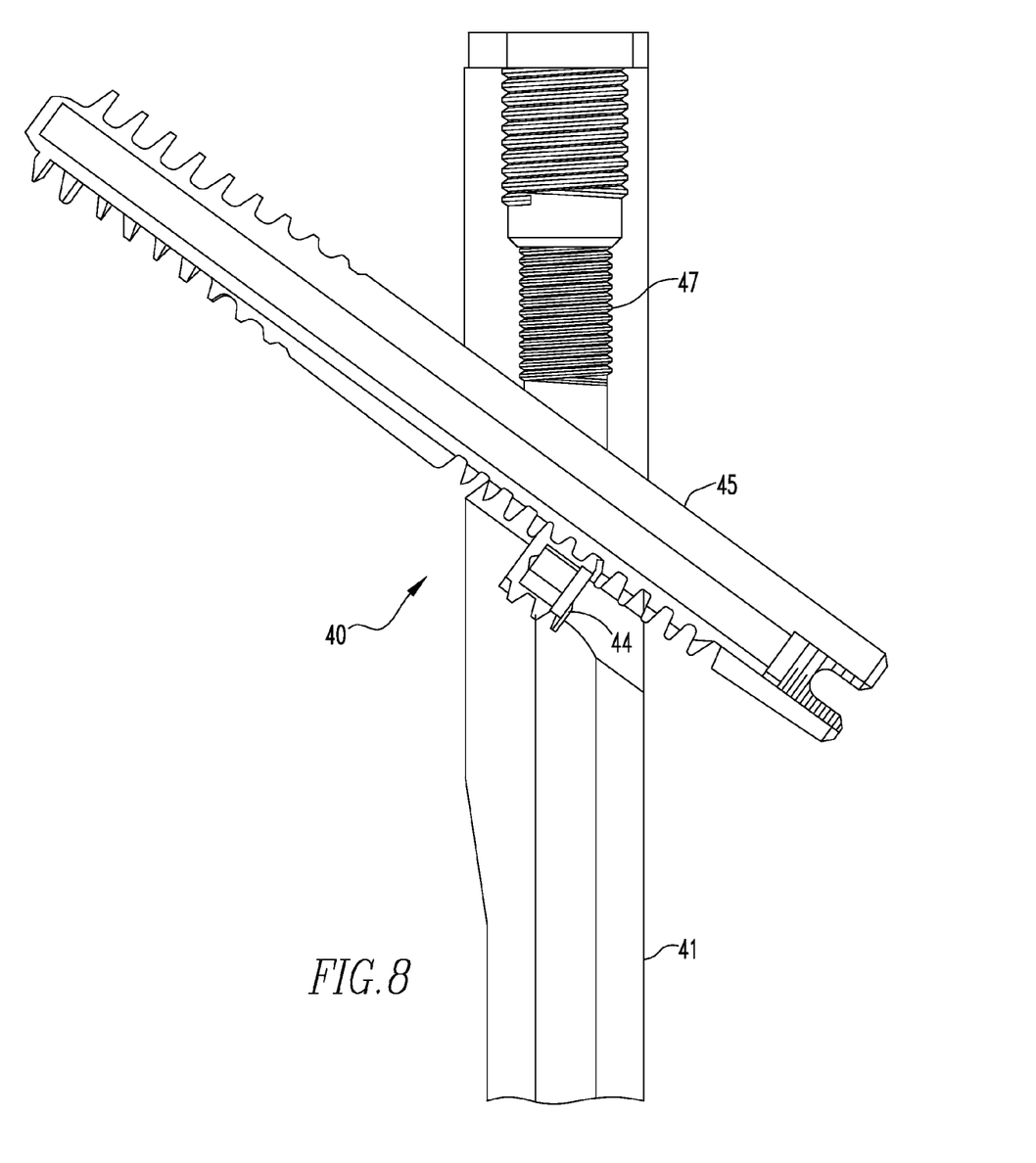
FIG. 8 is an anterior view of a fracture fixation system in a fifth embodiment.

FIGS. 7 and 8 illustrate a fracture fixation system 40 according to other embodiments of the invention. The fracture fixation system 40 includes an intramedullary device 41 and a compression member 44. The embodiment depicted in FIG. 7 includes engaging members 42 and interlock member 43, whereas the embodiment depicted in FIG. 8 includes only a single engaging member 45 and not an interlock member. Otherwise, the embodiments depicted in FIGS. 7 and 8 are the same. The intramedullary device is inserted first into the intramedullary canal of the femur. Then the bone is prepared for insertion of the engaging member 42 and the interlock member 43 or the single engaging member 45. Thereafter, the first compression member 44 engages the intramedullary device 41 and one of the members 42, 43, 45 to provide intraoperative compression and controlled movement of the multiple bone fragments. As an example, the first compression member 44 may have threads that engage both the intramedullary device 41 and one of the members 42, 43, 45.

In FIG. 7, the engaging member 42 and the interlock member 43 are adapted to gain purchase in bone fragments and interlock with one another to prevent rotation within the bone fragments. The members 42, 43 and the compression member 44 are configured so that compression member 44 interacts with a portion of the intramedullary device 41 and a portion of one of the members 42, 43. The adjustment or rotation of the compression member 44 controls the movement of the members 42, 43 relative to the intramedullary device 41 and provides intraoperative compression and controlled movement of the multiple bone fragments.

In FIG. 8, the engaging member 45 is adapted to gain purchase in bone fragments. The engaging member 45 may have an external shape that engages with an internal shape of the intramedullary device 41 to prevent rotation within the bone fragments. As examples, the intramedullary device 41 may have an internal square, hex, or octagon shape that receives an external square, hex, or octagon shape of the engaging member 45. The engaging member 45 and the compression member 44 are configured so that compression member 44 interacts with a portion of the intramedullary device 41 and a portion of the engaging members 45. The adjustment or rotation of the compression member 44 controls the movement of the engaging member 45 relative to the intramedullary device 41 and provides intraoperative compression and controlled movement of the multiple bone fragments.

In some embodiments, a fastener 47 is placed within the intramedullary device 41 to lock the engaging member in a specific location. For example, a screw may be placed within an internally threaded cannulated portion of the intramedullary device and threaded downward until the screw engages the engaging member 45.

Figure 9:
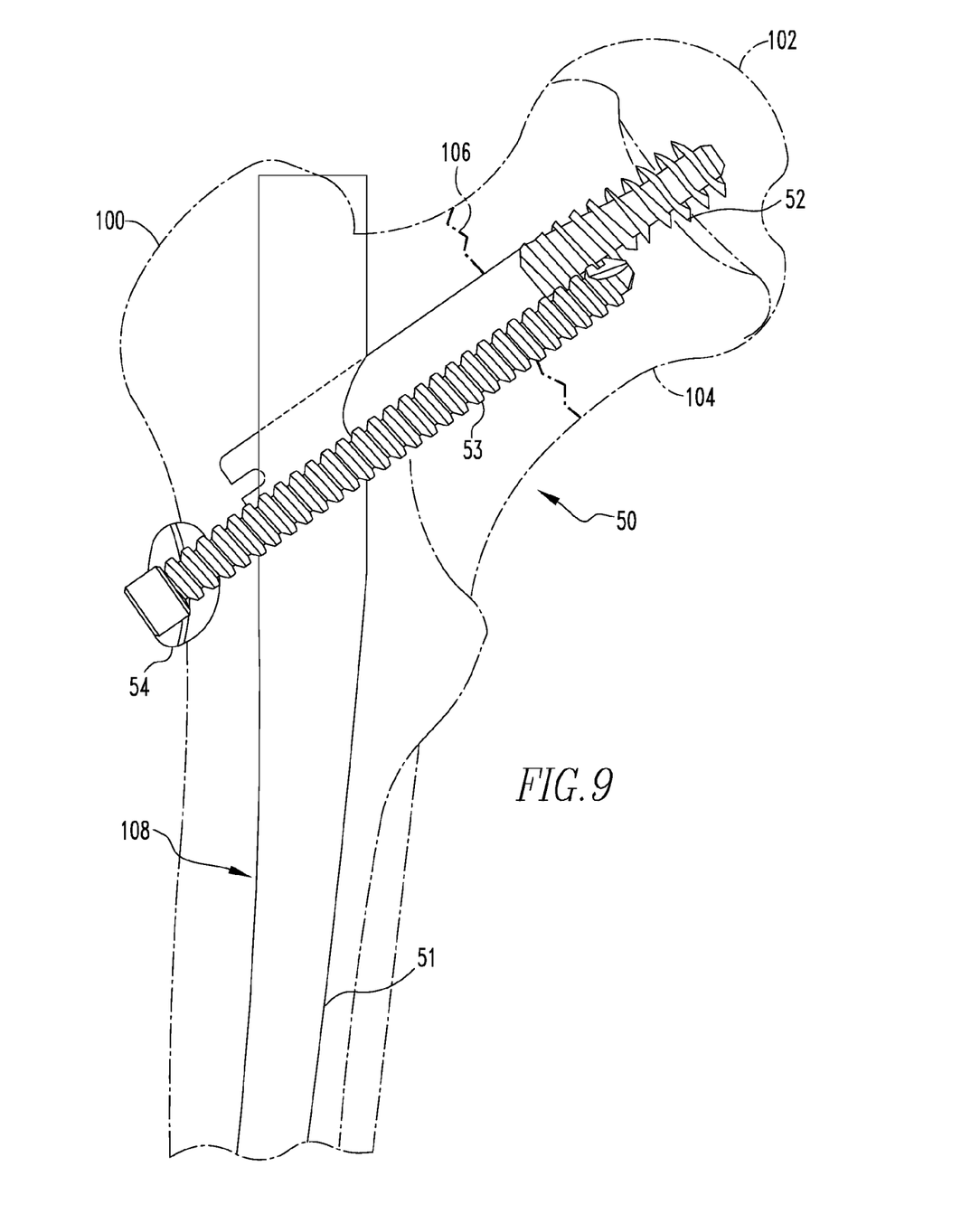
FIG. 9 is an anterior view of a fracture fixation system in a sixth embodiment.

FIG. 9 illustrates a fracture fixation system 50 according to another embodiment of the invention. The fracture fixation system 50 includes an intramedullary device 51, an engaging member 52 and an interlock member 53. FIG. 9 also illustrates a femur 100. The femur 100 includes a head 102, a neck 104, a fracture 106, and an intramedullary cavity 108. The intramedullary device 51 is placed into the intramedullary canal 108 of a femur 100. The engaging member 52 and the interlock member 53 are placed within the neck 104, across the fracture 106, and toward the head 102. A fastener 54 may rest on a surface of the femur 100 or sit on the outer or lateral portion of the intramedullary device 51. In the depicted embodiment, the fastener 54 is a nut. The fastener 54 is used to generate compression of the interlock member 53 and reduce the fracture when a torque is applied to nut 54. The intraoperative compression in this embodiment is achieved outside of the intramedullary device 51. In the depicted embodiment, the point of compression occurs at the point where the fastener 54 contacts the bone 100.

Alternatively, the fastener 54 is a washer and the interlock member 53 is rotated to apply compression. For example, a head 55 may be rotated such that threads of the interlock member 53 engage threads of the engaging member 52. As the threads engage, the head 55 presses upon fastener 54 and results in a compressive force being applied to the bone fragments.

Figure 10:
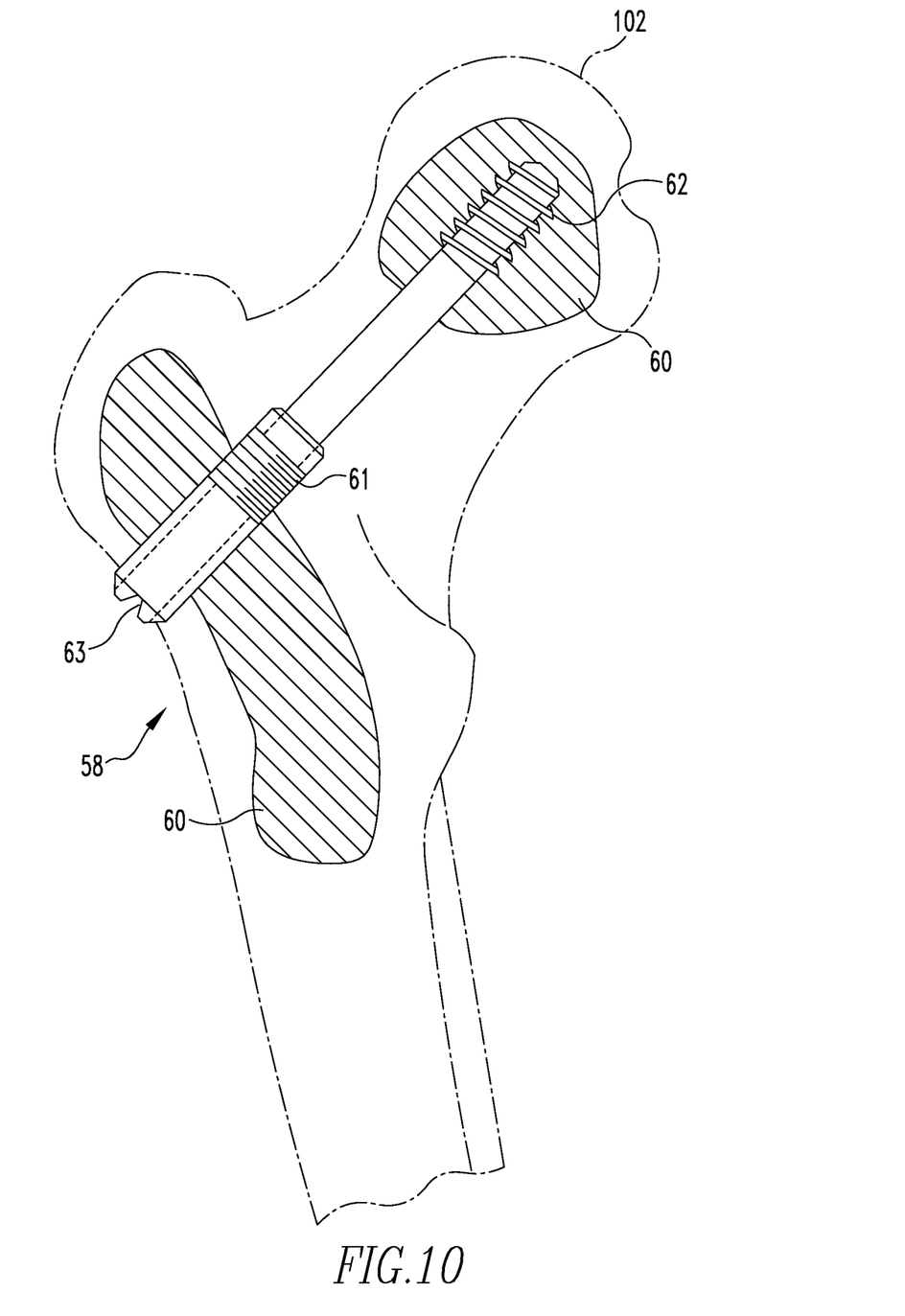
FIG. 10 is an anterior view of a fracture fixation system in a seventh embodiment.

FIG. 10 illustrates another embodiment of the invention in which a fracture fixation system 58 utilizes a deployable material 60, such as cement. The deployable material is capable of hardening after insertion into a predrilled area of the femoral head 102. To prepare for implantation of the fracture fixation system 58, a surgeon drills the desired area for placement of the deployable material and removes some bone material. Then the surgeon inserts the deployable material 60 into the area where the bone material was removed. After an amount of time necessary for the material to set or harden, the deployed material may be used to provide rigid fixation. The drill then is used again to drill through the now hardened deployable material 60 and prepare for insertion of engaging and compressing members. In the depicted embodiment, there is provided a barrel 61, an engaging member 62, and a compression member 63. The engaging member 62 screws into the head 102. As a torque is applied to the compression member 63, the compression member 63 causes the engaging member 62 to pull back in through the barrel 61 to compress or reduce the fracture.

Figure 11:
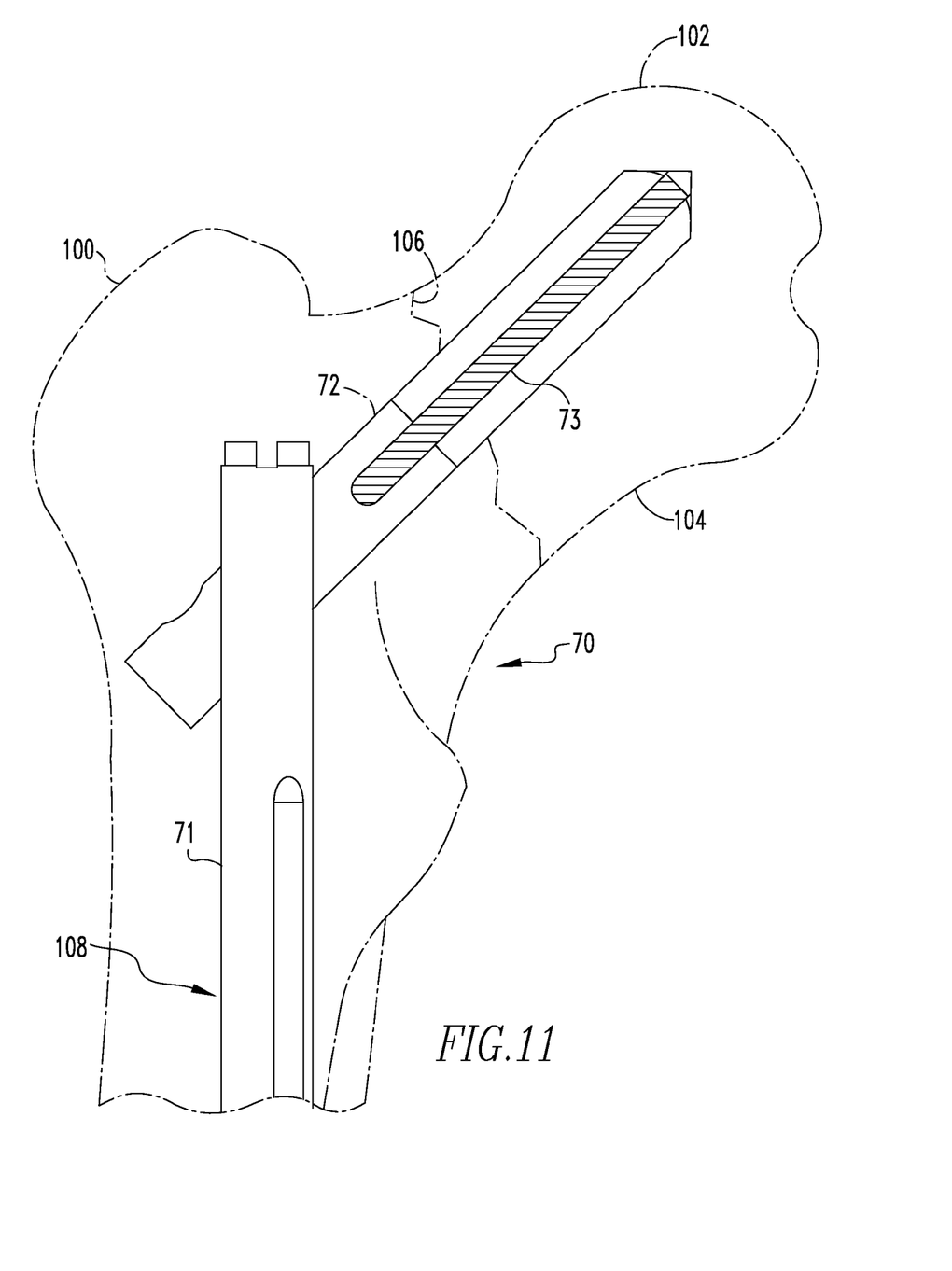
FIG. 11 is an anterior view of a fracture fixation system in a eighth embodiment.
Figure 12:
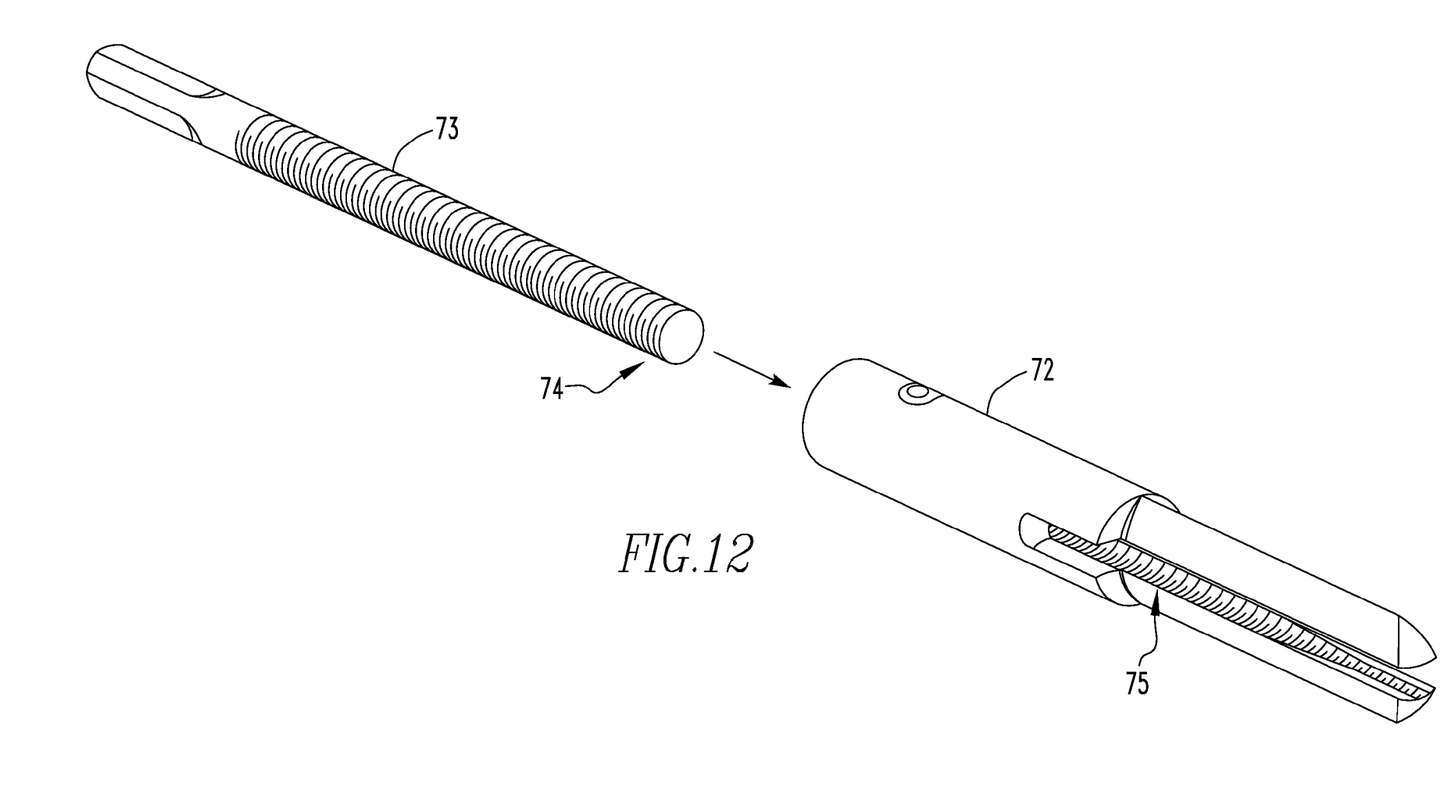
FIG. 12 is a detailed exploded view of an engaging member and a compression member.

FIGS. 11 and 12 illustrate a fracture fixation system 70 having an intramedullary device 71, an engaging member 72 and compression member 73. FIG. 11 also illustrates the femur 100, the femoral head 102, the femoral neck 104, the fracture 106, and the intramedullary cavity 108. The intramedullary device 71 is first inserted into the intramedullary cavity 108. Then the bone is prepared, typically by drilling, for the compression and engaging members 72, 73. The compression member 73 has a tapering depth thread as it moves toward a distal tip end 74. The compression 73 member threads into an inside 75 of the engaging member 72. As the thread depth decreases on the compression member 73, the change in depth of thread engagement causes the engaging member 72 to deploy radially outward providing a rigid fixation and anti-rotation. Alternatively, instead of tapering the thread depth one of ordinary skill in the art would understand to taper a diameter of the compressing member 73.

Figure 13:
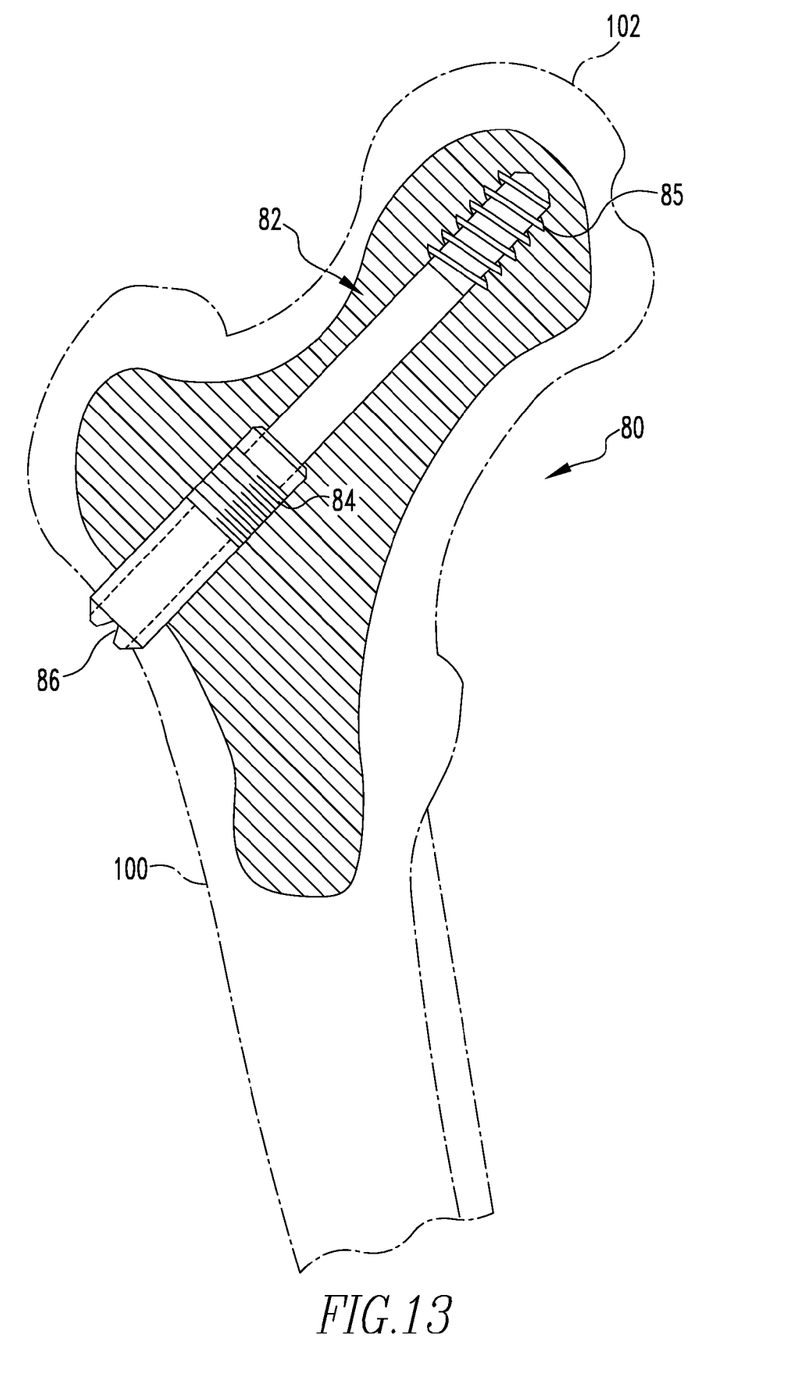
FIG. 13 is an anterior view of a fracture fixation system in a ninth embodiment.

FIG. 13 illustrates another embodiment of the invention in which a fracture fixation system 80 utilizes a deployable material 82, such as cement. The deployable material is capable of hardening after insertion into a predrilled area of the femoral head 102. To prepare for implantation of the fracture fixation system 80, a surgeon drills the desired area for placement of the deployable material and removes some bone material. Then the surgeon inserts the deployable material 82 into the area where the bone material was removed. After an amount of time necessary for the material to set or harden, the deployed material may be used to provide rigid fixation. The drill then is used again to drill through the now hardened deployable material 82 and prepare for insertion of engaging and compressing members. In the depicted embodiment, there is provided a barrel 84, an engaging member 85, and a compression member 86. The engaging member 85 screws into the head 102. As a torque is applied to the compression member 86, the compression member 86 causes the engaging member 85 to pull back in through the barrel 84 to compress or reduce the fracture. The method includes the steps of forming a cavity, injecting the deployable material to form a structural support, solidifying the deployable material, implanting a compression member, and adjusting the compression member.

The deployable material 82 may be resorbable or non-resorbable. Resorbable materials include, but are not limited to, polymeric materials, such as polyurethane, poly-alpha-hydroxy acids, polylactide and polyglycolide, including their copolymers, poly-(D,L-lactide-co-glycolide-) and polyglycolide-co-trimethylencarbonate; stereopolymers, such as poly-(L-lactide) or poly-L-lactic acid (PLA), poly-(L-CO-D, L-lactide) and poly-(D,L-lactide), polyglactic acid (PGA), a combination thereof (PLA/PGA) or any derivative, combination, composite, or variation thereof, poly-(D,L-lactide-co-glycolide) (PDLLA-co-PGA), poly-(L-lactide) (PLLA), polyglycolide-co-trimethylencarbonate, (PGA-co-TMC), poly-(L-CO-D,L-lactide), poly-(D,L-lactide), (PDLLA). The use of slow degrading and highly crystalline polymers, such as poly-(L-lactide) and poly(L-CO-D,L-lactide) stereocopolymers with a low D,L amount, amorphous polymers, such as poly-(L-CO-D,L-lactide) stereocopolymers with a high D,L amount and the purous poly-(D,L-lactide), or fast-degrading copolymers, such as poly-(D,L-lactide-co-glycolide) or polyglycolide-co-trimethylencarbonate, is envisioned and falls within the scope of the present invention. The use of injectable or crosslinkable polymers, including, but not limited to, photopolymerizable and chemically polymerizable polymers and polymers that harden in situ, is also encompassed by the present invention, including but not limited to the use of polymers of sebacic acid (SA), alone, or copolymers of SA and 1,3-bis(p-carboxyphenoxy)propane (CPP), or 1,6-bis(p-carboxyphenoxy)hexane (CPH), or poly (propylene fumarate) (PPF). Resorbable materials of the present invention are not limited to the foregoing and includes any fully or partially degradable or erodible in a body chemical composition or material suitable for use in the devices of the present invention, including but not limited to carbohydrates and derivatives thereof, such as such as cellulose or hyaluronic acid. Modifications of polymeric materials to adjust their structural, mechanical or chemical properties, or facilitate biological responses in tissues are envisioned and fall within the scope of the present invention.

The deployable material 82 may incorporate bioactive molecules that promote beneficial processes, such as healing, regeneration, bone regrowth and mineralization, and discourage undesirable processes, such as infection or inflammation. The bioactive molecules for incorporation into the deployable material include, but are not limited to, antibiotics; growth factors, including, but not limited to, insulin-like growth factors (IGF-I & II), transforming growth factors (TGFbs 1-3), fibroblast growth factors acidic and basic (aFGF & bFGF), platelet derived growth factor (PDGF), and bone morphogenetic proteins (BMPs); interleukins (IL), such as IL-1 b, IL-3 (Multi CSF), IL-4, IL-6, and IL-8; tumor necrosis factors TNF alpha and TNF beta; interferons (IFNs); colony stimulating factors; hormones, including but not limited to steroids, such as estrogen, and peptide hormones; anti-inflammatory molecules, including non-steroidal anti-inflammatory molecules; or any combination or variation thereof. The bioactive molecules are incorporated into resorbable adjunct stabilization devices according to any suitable method, including but not limited to, caging, impregnation, complexing, or chemical bonding, including the use of covalent and non-covalent bonds. Examples of beneficial modification with biologically active molecules include modification GRGD (Gly-Arg-Gly-Asp) peptide sequence to encourage host cell attachment and migration, and encapsulation of growth factors, such as TGF-1, which acts to direct cell migration and differentiation.

As examples, the deployable material may be a monomer material that polymerizes after insertion or a two component cement or epoxy. The deployable material's solidification may be catalyzed by increased temperature or humidity within the bone cavity. In one particular embodiment, micro-capsules may be filled with a liquid monomer and dispersed in the epoxy matrix. A catalyst is embedded in the epoxy that induces polymerization of the encapsulated monomer. When a crack occurs through the cured material, the micro-capsules are broken open. Capillary action draws the monomer into the crack and exposes it to the catalyst. The monomer then polymerizes. The polymerized material then binds two faces of the crack together. Alternatively, the deployable material may include polymethylacrylate (PMMA) and may be cured through the application of electromagnetic radiation, heat, or chemical catalyst.

Other materials that may be used to make the components of the fracture fixation system include titanium, titanium alloys, steel, cobalt-chromium alloys, tantalum, magnesium, peek, polyethylene, bioglass, brushite, hydroxyapatite, calcium sulfate, calcium phosphate, silicon oxide, silk, poly-alpha-hydroxy acids, polyglycols, polytyrosine carbonates, starch, gelatins, polysaccharides, polyurethanes, polyesters, polyphosphoesters, polyphosphates, polyphosphonates, modified protein, polyorthoesters, trimethylenecarbonate, polydioxanones, polycapropactones, cellulose, polylactides, polyglycolic acid, copolymers, any combination of the above, or other materials.

Figure 14:
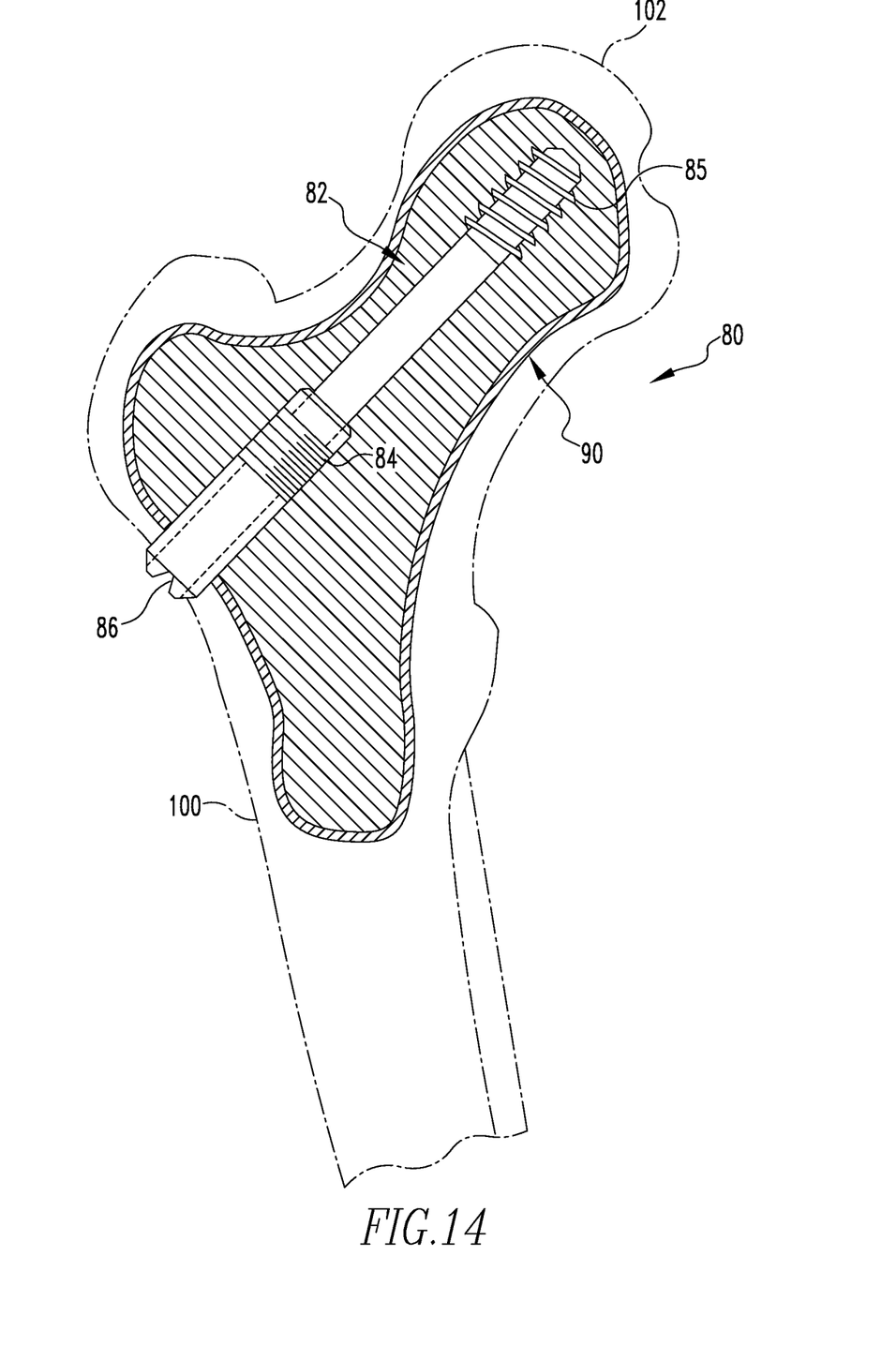
FIG. 14 is an anterior view of a fracture fixation system in a tenth embodiment.

FIG. 14 illustrates an embodiment similar to that of FIG. 13. The embodiment depicted in FIG. 14 includes all of the components of the fracture fixation system 80 but further includes a bag 90. The bag 90 receives the injected deployable material. The method includes the steps of forming a cavity, implanting the deployable material to form a structural support, solidifying the deployable material, implanting a compression member, and adjusting the compression member. The bag 90 is formed of a flexible, biocompatible polymer. For example, the bag 90 may be formed of polyester fibers, such as DACRON. DACRON is a registered trademark of Invista North America S.A.R.L. Corporation, Three Little Falls Centre, 2801 Centerville Road, Wilmington, Del. 19808. The bag 90 may be resorbable or non-resorbable.

In view of the foregoing, it will be seen that the several advantages of the invention are achieved and attained.

The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A fracture fixation system for a fractured bone having at least two bone fragments, the fracture fixation system comprising:
   a. an orthopaedic implant;
   b. an engaging member disposed relative to the orthopaedic implant, the engaging member including a deformable end portion adapted to gain purchase in at least one of the two bone fragments; and
   c. wherein the engaging member is cannulated and extends through the orthopaedic implant, and further comprising an elongate member slidably disposed within the engaging member, wherein the elongate member includes an enlarged end portion positioned in the deformable end portion of the engaging member, and further comprising a barrel positioned around the engaging member within the orthopaedic implant and a nut engaged to the elongate member against the barrel opposite the enlarged end portion, wherein a torque applied to the nut and against the barrel slides the elongate member within the cannulation so that the enlarged end portion of the elongate member outwardly deforms the end portion of the engaging member and the at least two bone fragments are placed in compression and prevented from rotating relative to the orthopaedic implant when the engaging member is in the at least one bone fragment and the orthopaedic implant is engaged to the other of the at least two bone fragments.

2. The fracture fixation system of claim 1, wherein the orthopaedic implant is selected from the group consisting of an intramedullary device, a compression plate, and a deployable material.

3. The fracture fixation system of claim 1, wherein the orthopaedic implant is an intramedullary device.

4. The fracture fixation system of claim 1, wherein the orthopaedic implant is a deployable material.

5. The fracture fixation system of claim 1, wherein the end portion of the engaging member comprises slits.

6. The fracture fixation system of claim 5, wherein the enlarged end portion of the elongate member has a shape selected from the group consisting of tapered and conical.

7. The fracture fixation system of claim 1, wherein the barrel, and wherein the engaging member is slidably positioned within the barrel;
   wherein the torque applied to the nut and slidably displaces the elongate member through the engaging member whereby the enlarged end portion of the elongate member outwardly deforms the end portion of the engaging member; and
   wherein the torque applied to the nut slidably displaces the engaging member through the barrel whereby the at least two bone fragments are placed in compression.

8. A fracture fixation system for a fractured bone having at least two bone fragments, the fracture fixation system comprising:
   a. an orthopaedic implant;
   b. an engaging member disposed relative to the orthopaedic implant, the engaging member including an end portion adapted to gain purchase in at least one of the two bone fragments; and
   c. wherein the orthopaedic implant is an intramedullary device and further comprising a nut and an elongate member having an enlarged end portion, the engaging member has flats along its shaft, a fastener engages the flats and the intramedullary device to prevent rotation and limit the sliding of the engaging member, the nut engaged with the engaging member and the elongate member, the engaging member is cannulated and extends through the intramedullary device, the elongate member slides within the cannulation, the enlarged end portion is received in the end portion of the engaging member, and the enlarged end portion is configured to apply a force to the engaging member to outwardly deform the end portion of the engaging member when a torque is applied to the nut so that the at least two bone fragments are placed in compression and prevented from rotating relative to the orthopaedic implant when the engaging member is in the at least one bone fragment and the orthopaedic implant is engaged to the other of the at least two bone fragments.

9. The fracture fixation system of claim 1, wherein the orthopaedic implant is a compression plate.

10. The fracture fixation system of claim 8, wherein the end portion of the engaging member comprises slits.

11. The fracture fixation system of claim 10, wherein the enlarged end portion of the elongate member has a shape selected from the group consisting of tapered and conical.

12. A fracture fixation system for a fractured bone having at least two bone fragments, the fracture fixation system comprising:
   a. an orthopaedic implant, wherein the orthopaedic implant in an intramedullary device;
   b. an engaging member disposed relative to the orthopaedic implant; and
   c. the system further comprising an interlock member threadingly engaged with the engaging member and with the engaging member and the interlock member extending through the intramedullary device, and a compression member that threadingly engages the interlock member and threadingly engages the intramedullary device, wherein rotation of the compression member provides controlled movement of the engaging member and the interlock member relative to the intramedullary device to provide intraoperative compression and controlled movement of the at least two bone fragments.

13. A fracture fixation system for a fractured bone having at least two bone fragments, the fracture fixation system comprising:
   a. an orthopaedic implant;
   b. an engaging member disposed relative to the orthopaedic implant, the engaging member including an end portion adapted to gain purchase in at least one of the two bone fragments; and
   c. wherein the orthopaedic implant is an intramedullary device and further comprising a compression member having a tapering depth thread toward a distal tip end and wherein the tapering depth thread engages an internal portion of the engaging member and is configured to apply a force to the engaging member to expand the end portion of the engaging member radially outwardly as the compression member is threaded toward the end portion of the engaging member to place the two bone fragments in compression and prevent the two bone fragments from rotating relative to one another when the end portion of the engaging member is in the at least one bone fragment and the orthopaedic implant is engaged to the other of the at least two bone fragments.

14. The fracture fixation system of claim 13, wherein the compression member has an external thread defining the tapering depth as the external thread extends toward the distal tip end of the compression member.

15. The fracture fixation system of claim 14, wherein the external thread defining the tapering depth is threadingly engaged with an internal thread extending along the internal portion of the engaging member; and
   wherein a change in the tapering depth of the external thread expands the end portion of the engaging member radially outwardly as the compression member is threaded toward the end portion of the engaging member.

16. A fracture fixation system for a fractured bone having at least two bone fragments, the fracture fixation system comprising:
   a. an orthopaedic implant;
   b. an engaging member disposed relative to the orthopaedic implant, the engaging member including an end portion adapted to gain purchase in at least one of the two bone fragments; and
   c. wherein the orthopaedic implant is an intramedullary device and further comprising a compression member having an external thread defining a tapering thread depth as the external thread extends toward a distal end of the compression member, the external thread defining the tapering thread depth threadingly engaged with an internal thread extending along a portion of the engaging member, and wherein a change in the tapering thread depth of the external thread expands the end portion of the engaging member radially outwardly as the compression member is moved through the end portion of the engaging member.

* * * * *